United States Patent [19]
Druais

[11] Patent Number: 5,351,925
[45] Date of Patent: Oct. 4, 1994

[54] DEVICE FOR SUPPORTING AND POSITIONING A MICROSCOPE

[75] Inventor: Hervé Druais, Seyssinet, France

[73] Assignee: Deemed International, France

[21] Appl. No.: 969,842

[22] PCT Filed: Jul. 15, 1991

[86] PCT No.: PCT/FR91/00583

§ 371 Date: Jun. 23, 1993

§ 102(e) Date: Jun. 23, 1993

[87] PCT Pub. No.: WO92/01963

PCT Pub. Date: Feb. 6, 1992

[30] Foreign Application Priority Data

Jul. 18, 1990 [FR] France .................. 90 09159

[51] Int. Cl.5 .................................................. A47H 1/10
[52] U.S. Cl. ............................................ 248/325; 248/123.1
[58] Field of Search ............. 248/550, 324, 325, 281.1, 248/123.1, 124; 359/382; 414/719

[56] References Cited

U.S. PATENT DOCUMENTS

| | | | |
|---|---|---|---|
| 3,809,454 | 5/1974 | Brambring | 359/382 |
| 4,344,595 | 8/1982 | Heller | 248/123.1 X |
| 4,531,816 | 7/1985 | Baumgartel | 359/382 |
| 4,684,088 | 8/1987 | Heller | 248/123.1 |
| 4,741,607 | 5/1988 | Heller | 248/123.1 |
| 4,867,405 | 9/1989 | Nakamura | 248/281.1 |
| 5,186,422 | 2/1993 | Nakamura | 359/382 |
| 5,205,522 | 4/1993 | Nakamura | 248/281.1 X |
| 5,213,293 | 5/1993 | Muentener | 248/123.1 |

FOREIGN PATENT DOCUMENTS

| | | | |
|---|---|---|---|
| 202399 | 11/1986 | European Pat. Off. | |
| 3744156 | 7/1989 | Fed. Rep. of Germany | 359/389 |
| 2593931 | 8/1987 | France | |

Primary Examiner—J. Franklin Foss
Attorney, Agent, or Firm—Gunn, Lee & Miller

[57] ABSTRACT

A device (2) for supporting and positioning a microscope, the device comprising a support suitable for being tied to a fixed frame of reference, and a plate suitable for supporting a microscope (17), an intermediate moving element (7) being connected firstly to said support (2) via a first series of motor-driven hinged members (6) of parallel type structure having three Cartesian XYZ degrees of freedom and to said plate via a second series of motor-driven members (9) gimbal-type structure providing three degrees of freedom in rotation, the device including control means generating control signals that are used by a computer for servo-controlling the displacement of the microscope (17).

12 Claims, 2 Drawing Sheets

DEVICE FOR SUPPORTING AND POSITIONING A MICROSCOPE

The present invention relates to a device for supporting and positioning a microscope. An application for such a device lies in the field of microsurgery, and also in numerous other fields requiring high accuracy work with the assistance of a microscope. Motor-driven devices are known in the state of the art for adjusting surgical microscopes in which the apparatus suspended vertically from a support or on a stand is capable of being displaced in six or seven degrees of freedom. However, when the portion of the object under observation is not plane, or when the surface in question is observed at a certain angle of incidence, displacement causes focus to be lost since the trajectories generated do not take place on the optical axis. It is then necessary to constantly readjust the focus of the microscope lens. This gives rise to manifest discomfort in use and is highly prejudicial during microsurgical operations.

Proposals have also been made in the prior art for devices in which the microscope is supported so as to be capable of pivoting about a first axis perpendicular to the optical axis and about a second axis that is substantially vertical. When the magnification of the microscope is very low, such an embodiment is acceptable. However, under all circumstances, rotation causes the observer to see the point of aim moving in the field of view. The user is thus continually constrained to recenter the field of view. In addition, focusing is maintained for certain types of displacement only.

Since considerable progress has been made in micromanipulation both in surgery and in other fields such as precision engineering, it has become clear that known types of microscope support suffer from drawbacks that handicap an operator. Part of an operator's attention and effort must be devoted to adjusting the positioning and focusing of the microscope.

To remedy those drawbacks, an object of the present invention is to provide a microscope support of great stability and of ergonomic design that facilitates positioning of the microscope by the operator. In addition, a preferred embodiment of the device makes it possible to control displacements of the microscope along trajectories that are monitored and controlled in a frame of reference that includes the line of sight. More particularly, the present invention provides a device for supporting and positioning a microscope, the device comprising a support suitable for being tied to a fixed frame of reference, and a plate suitable for supporting a microscope, an intermediate moving element being connected firstly to said support via a first series of motor-driven hinged members of parallel structure providing three Cartesian degrees of freedom and to said plate by a second series of motor-driven members of gimbal-type structure providing three degrees of freedom in rotation. In a particular embodiment, the device further includes control means generating control signals that are used by a computer for displacing the microscope in the frame of reference that includes the line of sight of said microscope in a plane perpendicular to the line of sight and/or around a sphere centered on the image focal point of the objective lens of the microscope and having a radius corresponding substantially to the focal length of said objective lens.

The operator is thus no longer required to take any action for controlling the focus or the trajectory of the microscope.

In a preferred embodiment, the series of motor-driven hinged members of parallel structure providing three Cartesian degrees of freedom is constituted by three arms movable in rotation about axes secured to said support, said axes being coplanar. The opposite ends of each of said three arms are connected to the moving element by means of respective link bars. Three actuators secured to the support control the movements of said three moving arms. The other series of motor-driven hinged members advantageously has three degrees of freedom in rotation about three perpendicular axes. That makes six degrees of freedom, namely three degrees of freedom in translation and three degrees of freedom in rotation.

This embodiment makes it possible to control the three basic degrees of freedom in parallel from actuators supported by the fixed portion of the device. This reduces inertia and the stresses acting on the moving portions. In addition, such parallel structures have great rigidity. This situation is naturally most advantageous since it makes it possible to improve the stability and the accuracy of the device.

In a preferred embodiment, the device includes a right control handle and a left control handle secured to said plate, each including three displacement sensors, a fourth displacement sensor measuring the displacement of the two handles relative to the plate. The signals generated by the sensors are processed to generate signals $M_{di}$, $M_{gi}$, and $M_y$ respectively representative of the displacements of the right handle, of the left handle, and of the rectilinear displacement of both handles, with i varying over the range 1 to 3 and designating the three directions of the measurement frame of reference. The signals are converted into translation speed information V and rotary speed information W in compliance with the following equations (where D is the distance between the handles):

$$V_{px} = \tfrac{1}{2}(M_{d1} + M_{g1}) \qquad W_{px} = \tfrac{1}{2}(M_{g2} - M_{d2})/D$$
$$V_{py} = M_y \qquad W_{py} = \tfrac{1}{2}(M_{d3} + M_{g3})$$
$$V_{pz} = \tfrac{1}{2}(M_{d2} + M_{g2}) \qquad W_{pz} = \tfrac{1}{2}(M_{d1} - M_{g1})/D$$

These speeds are expressed in a frame of reference parallel to that of the frame of reference of the handles, with the center of the frame of reference being situated on the line of sight. This speed information is made use of when controlling the movement of the microscope.

The device implemented in this way is very ergonomic and facilitates optimum utilization. In particular, the movements required for controlling the handles correspond substantially to the movements that the operator would make when displacing a non-servo-controlled microscope. In particular, since the control handles are disposed on the microscope-carrying plate, the operator physically feels the effect of action taken on the control handles. The operator is thus integrated in the system.

Advantageously, each of the control handles includes potentiometer sensors, one of said sensors measuring rotation of the handle about the axis that passes through both handles. The electrical signals from these sensors are converted into digital signals by an analog-to-digital converter.

Advantageously, the control means include a detector that generates a brake-release signal whenever the operator acts on said control means. The microscope is thus automatically stabilized as soon as the operator ceases to act on the controls, going through a stage in which all six axes are servo-controlled in position and then braked.

Advantageously, the translation speed signals and the rotation speed signals are filtered to limit variations to a threshold value. Unwanted displacements that could be dangerous in certain circumstances are thus avoided. Such movements could occur in the event of a clumsy action by the operator on the control means, in the event of control instructions that are incompatible with the mechanical strength of the device, or in the event of the control handles accidentally colliding with a person or an object.

In a particular embodiment, the device of the present invention includes a slow rectilinear displacement mode for the microscope in which the microscope moves within a frame of reference tied to the handles and in Cartesian mode, as a function of the forces exerted on at least one of the control handles. This constitutes an integrated puppet system. The operator can thus control displacements of very small amplitude with one hand only, leaving at least one hand free for the precision work in progress. Likewise, with a control pedal, it is possible to generate displacement in the frame of reference tied to the line of sight while leaving both hands free.

In another variant, the device includes a slow spherical displacement mode for the microscope in which the microscope is displaced over a sphere centered on the point of aim, as a function of forces exerted on at least one of the control handles. Such spherical displacement may be controlled either from the control handles or else from an additional pedal. The parameter corresponding to the focal length defining the radius of the displacement sphere is stored by the computer in a parameter file during configuration of the system.

The present invention is described in greater detail below with reference to the accompanying drawings, in which:

FIG. 1 is a simplified view of an embodiment of the device of the invention.

Figure 1:
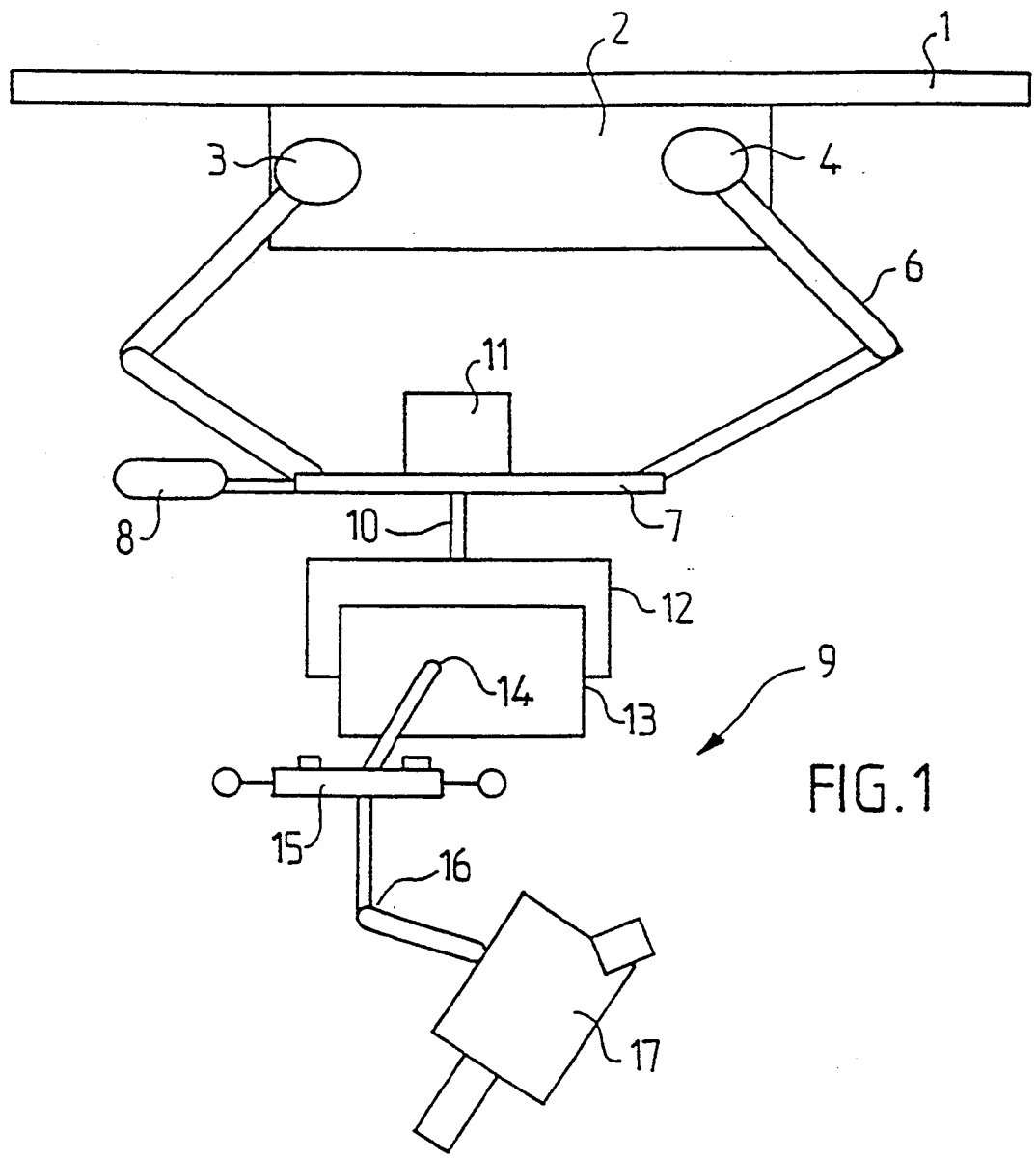
FIG. 1 is a diagrammatic view of the device.

It is fixed to the ceiling, e.g. of a microsurgery operating theater, by means of a prepositioning rail (1). This prepositioning rail enables the entire device to be positioned over the operating field. The prepositioning rail (1) guides a support (2) that includes three motors (3, 4, 5) controlling the movements of a first series (6) of hinged members. This first series of hinged members is constituted by a "delta parallel" three-axis system that is described in greater detail with reference to FIG. 1. It is connected to an intermediate moving element (7). This intermediate element (7) moves parallel to the support (2), and thus in a horizontal plane, in most cases. It is provided with a prepositioning handle (8) enabling the entire device to be displaced along the guide rail (1). The intermediate moving element (7) supports the second series of hinged members (9) that include three orthogonal pivot axes. The first of these axes is a vertical axis (10) controlled by a motor (11) disposed on the intermediate moving element (7). This vertical axis (10) is secured to a frame (12) having a perpendicular axis of rotation (13). This axis is connected to an intermediate part supporting two motors that control movements about two axes (13, 14) that are perpendicular to each other and to the vertical axis (10). The control means (15) are secured to the order 6 axis (14) perpendicular to the order 4 axis (13) and the order 5 axis (10) mentioned above. The microscope (17) is secured to the axis (14) by means of an additional rotary axis of order 7. This prepositioning order (16) makes it possible to adjust the line of sight depending on the type of operation that is envisaged.

Figure 3:
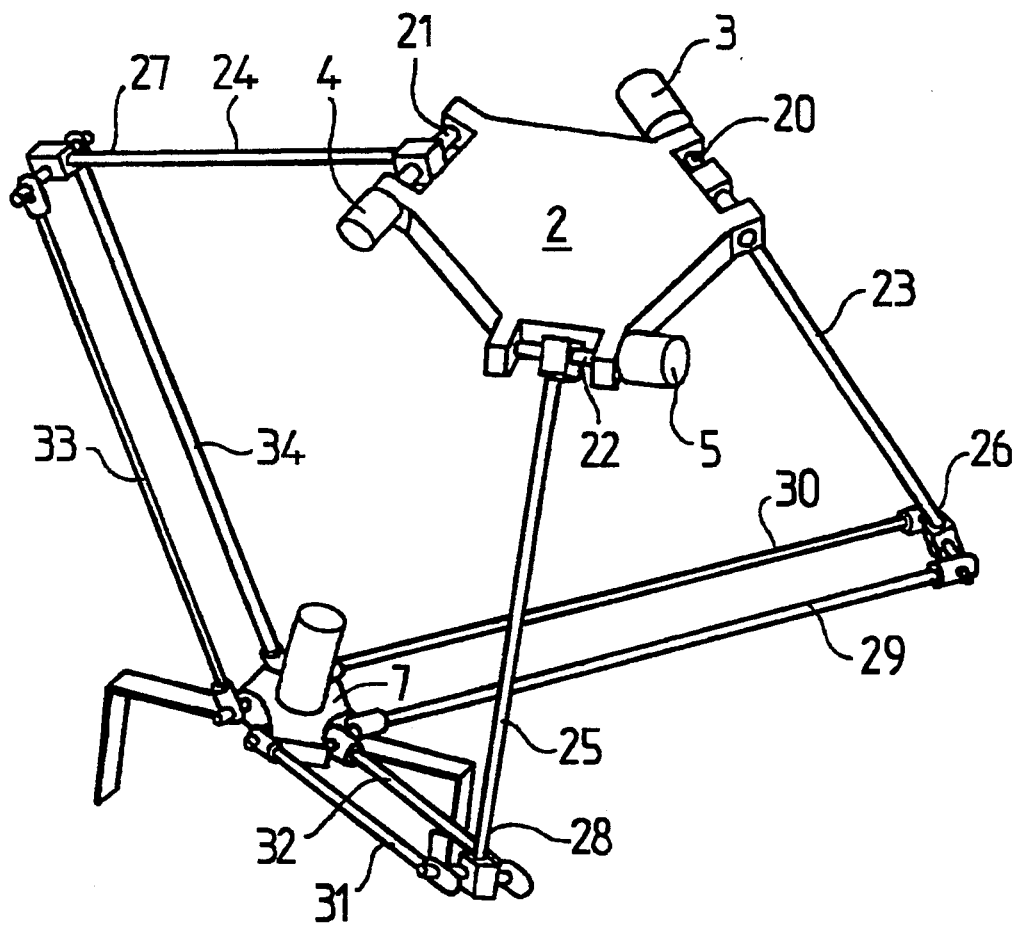
FIG. 3 is a detailed view of the first series of hinged members.

FIG. 3 is a detailed view showing the way in which the first series of hinged members (6) is embodied.

The support (2) includes three motors (3, 4, 5) each including a fixed portion secured to the support, and having respective shafts (20, 21, 22) that are coplanar. Control arms (23, 24, 25) are secured to respective ones of said shafts (20, 21, 22). These arms are rigidly mounted on said shafts, with their longitudinal axes extending perpendicularly to the corresponding shafts. The opposite ends (26 to 28) of the arms (23 to 25) are secured to respective pairs of link arms (29, 30), (31, 32), and (33, 34) by two double hinges formed by two mutually perpendicular gimbal-type axes. Each of the pairs of link arms is also connected to the intermediate moving element (7) by pairs of hinges formed by two mutually perpendicular gimbal-type axes. The 120° disposition of the hinged arms is given by way of preferred example since that configuration gives good rigidity. Nevertheless, the invention is not limited to that embodiment and numerous other embodiments could be envisaged.

Figure 2:
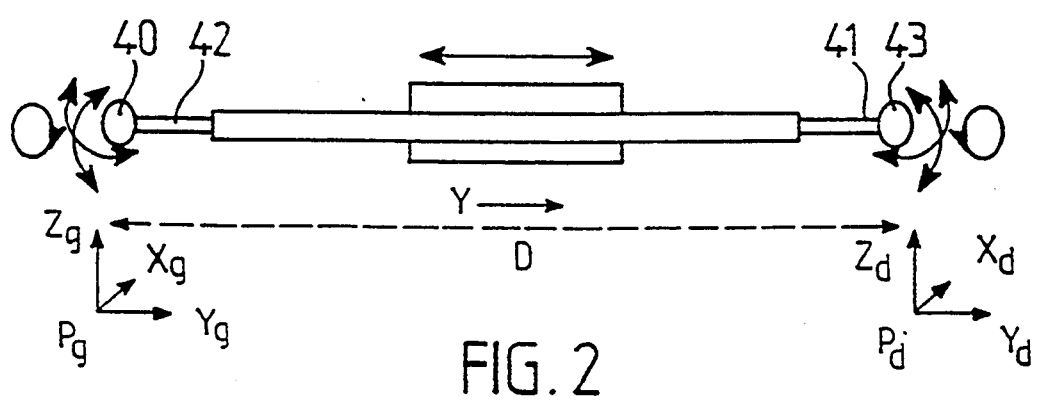
FIG. 2 is a diagrammatic view of the control means.

FIG. 2 is a detailed view of one embodiment of the control means, using a left handle (40) and a right handle (41). As mentioned above, the control means are secured to the order 6 axis (14) so as to transmit ergonomic impressions to the operator.

The handles are of the "joystick" type and they act differentially. Each of them comprises a stick (42, 43) mounted on a ball-and-socket bearing allowing angular displacements in two perpendicular planes. These displacements are symbolized in FIG. 2 by arrows. The sticks can also be rotated about their own longitudinal axes. In addition, the handles may be displaced simultaneously in translation along the longitudinal axis.

The displacements of the sticks (42, 43) are transmitted to potentiometers which deliver analog signals. The potentiometer values are converted into digital signals by a 12-bit analog-to-digital converter and they are processed digitally to obtain speeds of translation and of rotation. Naturally, it is possible to envisage using other types of control means, implementing other sensors that are known in the state of the art. The speeds are determined by the following relationships:

$$V_{px} = \tfrac{1}{2}(M_{d1} + M_{g1}) \quad W_{px} = \tfrac{1}{2}(M_{g2} - M_{d2})/D$$
$$V_{py} = M_y \quad W_{py} = \tfrac{1}{2}(M_{d3} + M_{g3})$$
$$V_{pz} = \tfrac{1}{2}(M_{d2} + M_{g2}) \quad W_{pz} = \tfrac{1}{2}(M_{d1} - M_{g1})/D$$

where:

---

$M_{d1}$ = displacement of the right handle 43 along the axis $OX_d$ $M_{g1}$ = displacement of the left handle along the axis $OX_g$ -continued $M_{d2}$ = displacement of the right handle 43 along the axis $OZ_d$
$M_{d3}$ = rotation of the right handle 43 along the axis $OY_d$
$M_y$ = displacement in translation of the control means along the longitudinal axis Y.

$M_{g2}$ = displacement of the left handle along the axis $OZ_g$
$M_{g3}$ = rotation of the left handle along the axis $OY_g$ The digital data is processed so as to clip values exceeding an adjustable threshold and to clip variations exceeding another adjustable threshold, thereby avoiding displacements that are too sudden which could exceed the mechanical strength of the device, of the microscope, or of the user.

Signal processing is performed non-linearly, normalized on speed, so as to enable not only accurate displacement at very slow speeds, but also displacement at high speeds.

The actuators of the hinged members are controlled by a computer that performs the following operations:
  acquiring analog control signals as generated by the control handles;
  converting said signals from analog form to digital form;
  filtering the digital signals to eliminate untimely data and to deliver digital signals that correspond to desired speeds in translation and in rotation;
  acquiring signals corresponding to the position of the system at an instant T and transferring them by the direct geometrical model to obtain positions in Cartesian space;
  using the inverse dynamic model on the basis of present Cartesian positions and of desired rotary and Cartesian translation speeds to obtain movement references for the system at instant T;
  filtering to eliminate untimely data;
  controlling the laws of motion of the servo-control systems;
  digital-to-analog conversion of the movement references; and
  controlling the ergonomic controls of the system.

These signals control the movements of the actuators for the hinged members. The computer also performs other functions such as controlling safety systems, and calculating the position and the displacement of the microscope in the fixed frame of reference, or in a frame of reference determined by the operator.

In the example described, the computer is constituted by a conventional type of microcomputer connected to electronic circuits for acquiring signals and to a specialized axis control card (CAID) produced by DMD, to a control panel, and to a power stage that delivers the reference signals.

The computer manages three control modes. The "braked axis" first mode is the default mode in the absence of any action on the control members.

The "rapid displacement" second mode enables the operator to control displacements of the microscope at speeds proportional to the displacements applied to the handles and to the rectilinear displacement sensor along the longitudinal axis. It is controlled by the handles acting in differential manner for the translation and rotary controls. The maximum authorized speed is adjustable by means of a potentiometer disposed on the control panel. This parameter is left in part to the opinion of the operator. This control mode is possible only so long as the operator is acting physically on the control handles, since otherwise the device returns automatically to its "braked axis" mode. Action of the operator is detected by sensors integrated in the control handles.

The "slow displacement" third mode is a mode enabling the robot to be displaced along the directions XYZ of a Cartesian frame of reference tied to the line of sight of the microscope. It can be controlled either by the right handle, or by the left handle, or by an accessory pedal.

The computer makes use of the signals coming from the control handles or the pedal to deliver reference signals corresponding to plane trajectories perpendicular to the line of sight or to spherical trajectories about the aiming point, over a sphere whose radius corresponds to the focus distance and to translation displacements along the line of sight, as a function of actions taken on the control handles or on the pedal. Rectilinear and spherical modes are complementary to each other.

The present invention has been described above by way of non-limiting example. The person skilled in the art will naturally be able to make numerous variants without thereby going beyond the ambit of the invention.

I claim:

1. A device for supporting and positioning a microscope, the device comprising a support suitable for being tied to a fixed frame of reference, and a plate suitable for supporting a microscope, an intermediate moving element being connected firstly to said support via a first series of parallel motor-drive hinged members having three degrees of freedom and to said plate via a second series of motor-driven members, the device including control means generating control signals that are used by a computer for servo-controlling the displacement of the microscope.

2. A device according to claim 1, characterized in that the first series of motor-driven hinged members is constituted by three arms movable in rotation about shafts secured to said support, said shafts being coplanar, the opposite ends of each of said arms being connected to the moving element via at least one respective link bar, three actuators secured to the support controlling the movements of said moving arms.

3. A device according to claim 1 or 2, characterized in that the control means are constituted by a right handle and a left handle secured to said plate, each including three displacement sensors, a fourth displacement sensor measuring the displacement of the two handles relative to the plate, the signals generated by the sensors being processed to generate signals $M_{di}$, $M_{gi}$, and $M_y$ respectively representative of the displacements of the right handle, of the left handle, and of the rectilinear displacement of both handles, where i lies in the rage 1 to 3 which designate the three directions of the measurement frame of reference, said signals being converted into translation speed data V and rotation speed data W in application of the following equations:

$$V_{px} = \tfrac{1}{2}(M_{d1} + M_{g1}) \qquad W_{px} = \tfrac{1}{2}(M_{g2} - M_{d2})/D$$
$$V_{py} = M_y \qquad W_{py} = \tfrac{1}{2}(M_{d3} + M_{g3})$$
$$V_{pz} = \tfrac{1}{2}(M_{d2} + M_{g2}) \qquad W_{pz} = \tfrac{1}{2}(M_{d1} - M_{g1})/D$$

said speed being expressed in a frame of reference parallel to the handle frame of reference, the center of said frame of reference being situated on the line of sight, said speed data being used to control the movements of the microscope.

4. A device according to claim 3, characterized in that each of the control handles includes potentiometer sensors, one of said sensors measuring rotation of the handle about the axis passing both handles.

5. A device according to claim 1 characterized in that the control means includes a detector which generates a signal for deactivating the braked position whenever the operator acts on said control means.

6. A device according to claim 3 characterized in that the transaction speed and rotary speed signals are filtered to limit variations to a threshold value.

7. A device according to claim 2 characterized in that said device further includes a slow rectilinear displacement mode for the microscope in which the microscope moves in a frame of reference tied to the frame of reference of the handles, as a function of the forces exerted on one of the control handles or on a pedal.

8. A device according to claim 1 characterized in that it includes a spherical slow displacement mode for the microscope in which the microscope moves over a sphere centered on the aiming point, as a function of the action taken on at least one of the control handles or on a control pedal.

9. A device according to claim 1 characterized in that it includes an emergency stop control enabling the hinged means to be folded up quickly.

10. A device according to claim 2 characterized in that the control means includes a detector which generates a signal for deactivating the braked position whenever the operator acts on said control means.

11. A device according to claim 1 characterized in that said device further includes a slow rectilinear displacement mode for the microscope in which the microscope moves in a frame of reference tied to the frame of reference of the handles, as a function of the forces exerted on one of the control handles or on a pedal.

12. A device according to claim 3 characterized in that said device further includes a slow rectilinear displacement mode for the microscope in which the microscope moves in a frame of reference tied to the frame of reference of the handles, as a function of the forces exerted on one of the control handles or on a pedal.

* * * * *